(12) United States Patent
Al-Khattaf et al.

(10) Patent No.: US 8,779,227 B2
(45) Date of Patent: Jul. 15, 2014

(54) METHOD OF MAKING DIETHYLBENZENE

(75) Inventors: Sulaiman S. Al-Khattaf, Dhahran (SA); Taiwo Odedairo, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 125 days.

(21) Appl. No.: 13/604,530

(22) Filed: Sep. 5, 2012

(65) Prior Publication Data

US 2014/0066679 A1    Mar. 6, 2014

(51) Int. Cl.
*C07C 2/66* (2006.01)
*C07C 1/24* (2006.01)

(52) U.S. Cl.
USPC .......................................... 585/467; 585/469

(58) Field of Classification Search
USPC .................................. 585/469, 467
See application file for complete search history.

(56) References Cited

U.S. PATENT DOCUMENTS 5,811,613 A * 9/1998 Bhat et al. ..................... 585/467
2011/0201864 A1   8/2011 Al-Khattaf et al.

FOREIGN PATENT DOCUMENTS

CN     1546236 A    11/2004
JP     2000281595 A  10/2000

OTHER PUBLICATIONS

S. Al-Khattaf, N. M. Tutor and S, Rabin, "Ethylbenzene Transformation over a ZSM-5-Based Catalyst in a Riser. Simulator", *Ind. Eng. Chem. Res.*, 2009, 46 (6), pp. 2836-2843.
T. Odedairo and S. Al-Khattaf, "Kinetic analysis of benzene ethylation over ZSM-5 based catalyst in a fluidized-bed reactor", *Chemical Engineering Journal*, vol. 157, Issue 1, Feb. 2010, pp. 204-215.
T. Odedairo and S. Al-Khattaf, "Ethylation of benzene; Effect of zeolite acidity and structure", *Applied Catalysis A: General*, vol. 385, Issues 1-2, Sep. 15, 2010, pp. 31-45.

* cited by examiner

*Primary Examiner* — Thuan D Dang
(74) *Attorney, Agent, or Firm* — Richard C. Litman

(57) ABSTRACT

The method of making diethylbenzene selectively produces diethylbenzene by reacting ethylbenzene and ethanol over a zeolite catalyst, such as ZSM-5. The zeolite catalyst is first heated in argon gas within a reaction chamber. The zeolite catalyst is then selectively coked with a precursor mixture of ethylbenzene and ethanol. Argon gas is then flowed over the coked zeolite catalyst, and a reaction mixture of ethylbenzene and ethanol is injected into the reaction chamber to produce diethylbenzene, which is then removed from within the reaction chamber.

16 Claims, 2 Drawing Sheets

METHOD OF MAKING DIETHYLBENZENE

BACKGROUND OF THE INVENTION

1. Field of the Invention

The present invention relates generally to the manufacture of diethylbenzene, and particularly to a method of making diethylbenzene by reacting ethylbenzene and ethanol over a zeolite catalyst that has been pre-treated by coking the catalyst with an aromatic, an alcohol, or both to increase selectivity.

2. Description of the Related Art

Aromatic conversion reactions are of great industrial interest and importance. Such reactions include alkylation and transalkylation used to produce alkylaromatics, such as ethylbenzene, diethylbenzene, ethyltoluene, cumene and higher aromatics. Dialkylbenzenes, such as xylene and diethylbenzene, are of particular importance, as they are used for the production of polyesters, solvents, photodevelopers and antioxidants. Diethylbenzene, in particular, is an important raw material for conversion divinyl benzene monomer, and is also used in refineries for the separation of close boiling isomers. Diethylbenzenes are also used as solvents and precursors for cross-linking agents in producing resins.

A wide variety of reactor systems have been developed for carrying out aromatic conversion reactions. Conventional aromatic conversion systems include fixed bed reactors, such as multi-tubular fixed bed reactors, and fluidized bed reactors. The alkylation of ethylbenzene with ethanol is a reaction that is of immense industrial importance. This reaction provides an alternate route for producing various isomers of diethylbenzene (ortho-, meta- and para-diethylbenzene). Due to the rapid development of biochemical engineering technology, the cost of obtaining ethanol has greatly decreased. Thus, the direct use of ethanol in manufacturing diethylbenzene is of economic benefit to those countries where biomass-derived alcohol is readily available for manufacturing chemicals. Additionally, in situ dehydration of alcohols leads to prolonged catalyst activity, since the water of reaction suppresses coke formation, which is in contrast to vapor phase alkylation with ethylene at higher temperatures, where significant coke formation typically occurs.

Alkylation of ethylbenzene to diethylbenzene is commonly performed as an acid-catalyzed process. Diethylbenzene is conventionally synthesized by using existing alkylation catalysts, such as $AlCl_3$, $HF$, $BF_3$, and the like. Due to the strong acidity of these catalysts, disposal of the selected catalyst causes serious environmental pollution, along with corrosion of equipment used during the manufacturing process.

Thus, a method of making diethylbenzene solving the aforementioned problems is desired.

SUMMARY OF THE INVENTION

The method of making diethylbenzene involves reacting ethylbenzene and ethanol over a zeolite catalyst, such as ZSM-5. The zeolite catalyst is first heated in argon gas within a reaction chamber. The zeolite catalyst is then selectively coked with an aromatic, an alcohol, or both, preferably a precursor mixture of ethylbenzene and ethanol. Argon gas is then flowed over the coked zeolite catalyst, and a reaction mixture of ethylbenzene and ethanol is injected into the reaction chamber to produce diethylbenzene, which is then removed from within the reaction chamber.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
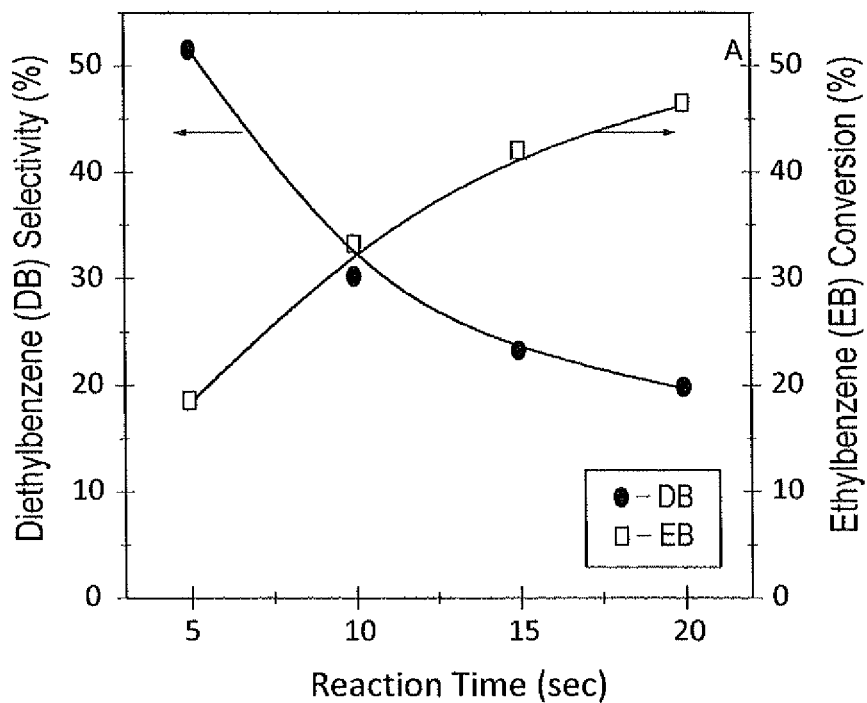
FIG. 1 is a graph illustrating ethylbenzene conversion and diethylbenzene selectivity as a function of reaction time at 400° C. reaction temperature without zeolite pretreatment.

The method of making diethylbenzene relates generally to the manufacture of diethylbenzene, and particularly to a method of making diethylbenzene by reacting ethylbenzene and ethanol over a zeolite catalyst. The zeolite catalyst is first heated in argon gas within a reaction chamber. The zeolite catalyst may be one of mordenite, beta, ZSM-5, ZSM-11, ZSM-12, ZSM-22, ZSM-23, SAPO-5, SAPO-34, SAPO-11, MAPO-36 zeolites or the like, and preferably has a silica-to-alumina molar ratio ($SiO_2$:$Al_2O_3$) between about 23 and about 80. In the preferred embodiment, ZSM-5 is used as the zeolite catalyst. During pretreatment, the zeolite catalyst is preferably heated at a temperature of approximately 620° C. for approximately 15 minutes in the argon gas within the reaction chamber.

Any suitable type of reactor having a reaction chamber, a gas inlet and a gas outlet may be utilized, such as a riser simulator or fast fluidized-bed reactor. Fast fluidized-bed reactors typically include a metallic gasket that seals a pair of chambers, and an impeller located within an upper chamber. Upon rotation of a shaft, gas is forced outward from the center of the impeller towards the walls of the chamber. This creates a lower pressure in the center region of the impeller, thus inducing a flow of gas upward through a catalyst chamber from the bottom of the reactor, where the pressure is slightly higher. The impeller provides a fluidized-bed of catalyst particles, as well as intense gas mixing inside the reactor. Preferably, such a reactor is used in the present method of manufacturing diethylbenzene.

Following heating of the zeolite catalyst in the argon gas, the zeolite catalyst is then selectively coked with an aromatic, and alcohol, or a mixture of an aromatic and an alcohol, preferably in a ratio between 1 to 1 and 1 to 6. Suitable aromatics include benzene, ethylbenzene, and diethylbenzene, or a mixture thereof. Suitable alcohols include ethanol, methanol, isopropanol, and butanol, or a mixture thereof. A preferred pretreatment mixture for the coking process is a mixture of ethylbenzene and ethanol. Coking (the process of depositing a carbonaceous material on the catalyst) is normally avoided with zeolite catalysts, since excessive coke formation shortens the life of the catalyst and may require regenerating the catalyst. Nevertheless, the present inventors have found that the coking pretreatment process enhances selectivity for the formation of diethylbenzene, including all three isomers. The coking process is preferably carried out in the vapor phase. The amount of carbon deposited as coke on the zeolite catalyst is preferably in the range of about 0.7 wt % to about 1.5 wt %. In the preferred embodiment, the amount of carbon in the deposited coke on the zeolite catalyst is preferably approximately 1.0 wt %. The ethylbenzene and ethanol are preferably provided in a molar ratio of between 1 to 1 and 1 to 6. The pretreatment of the catalyst is preferably carried out at a reaction temperature between approximately 250° C. and approximately 400° C. for a reaction time between about 5 seconds and about 20 seconds.

Argon gas is then flowed over the coked zeolite catalyst, and a reaction mixture of ethylbenzene and ethanol is injected into the reaction chamber to produce diethylbenzene, which is then removed from within the reaction chamber. The reaction temperature is preferably between approximately 250° C. and approximately 400° C. at a gas pressure between approximately 1.0 atmospheres and approximately 5.0 atmospheres. The ethylbenzene and ethanol are preferably provided in a molar ratio of between 1 to 1 and 1 to 6.

The injected feed stream, formed from the mixture of ethylbenzene and ethanol, provides effective ethylation of the ethylbenzene into a dialkylbenzene, namely diethylbenzene. The stream is preferably reacted in the vapor phase. The alkylation reaction is found to yield a product having a high diethylbenzene content and a low benzene content.

Example 1

In a first experimental example, a dry powder of the proton form of ZSM-5, having a silica-to-alumina molar ratio of 80, was pressed in a round steel die under high pressure to produce a disk, which was then broken into small pieces that were sieved to produce granules ranging in size from 1.0 to 1.5 mm The zeolite catalysts were tested for alkylation reaction using an ethylbenzene and ethanol feed mixture with a molar ratio of 1:1 in order to demonstrate the effectiveness of the catalysts for ethylbenzene conversion and production of diethylbenzene. For each catalyst, 80 mg of the catalyst was weighted and loaded onto a riser simulator basket. The system was then sealed and tested for any pressure leaks by monitoring the pressure changes in the system. The pretreated ZSM-5 was prepared as follows. The catalyst was activated for 15 minutes at 620° C. in a stream of argon. The pretreatment of the catalyst was carried out using a mixture of ethylbenzene and ethanol (200 microliters) in a molar ratio of 1:1 and at a reaction temperature of 400° C. for a reaction time of 20 seconds. Thereafter, the system was purged with argon for 10 minutes before the start of the reaction. Table 1 below gives information on the textural properties and the quantitative evaluation of the FT-IR spectra of the catalyst, both before and after pre-treatment.

TABLE 1

Properties of ZSM-5 catalysts

| Catalyst | Surface area (m$^2$/g) | Bronsted site (mmol pyridine/g) | Lewis site (mmol pyridine/g) |
| --- | --- | --- | --- |
| ZSM-5 (untreated) | 358 | 0.3920 | 0.1743 |
| ZSM-5 (pretreated) | 346 | 0.3661 | 0.1767 |

Catalytic experiments were carried out in the riser simulator with 200 microliters of the feed mixture of ethylbenzene with ethanol in a molar ratio of 1:1, injected directly into the reactor via a loading syringe, for reaction times of 10, 15 and 20 seconds at 400° C. The thermodynamic equilibrium composition of the three produced isomers at 400° C., for a reaction time of 20 seconds, for the catalyst, both without pretreatment and after pretreatment, are as follows: ortho-diethylbenzene:meta-diethylbenzene:para-diethylbenzene=12:60:28 and 10:61:29, respectively.

The vacuum box of the reactor was heated to 250° C. and evacuated to a pressure of 0.5 psi to prevent any condensation of hydrocarbons inside the box. The heating of the riser simulator was conducted under a continuous flow of inert gas (i.e., argon), and it takes a few hours until thermal equilibrium is finally attained.

Figure 2:
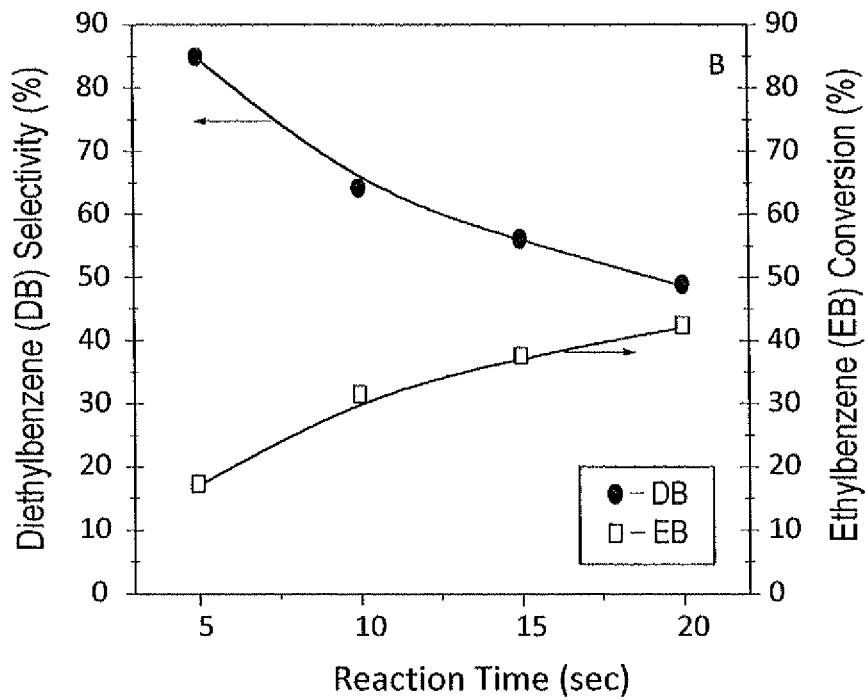
FIG. 2 is a graph illustrating ethylbenzene conversion and diethylbenzene selectivity as a function of reaction time at 400° C. reaction temperature following zeolite pretreatment in accordance with a method of making diethylbenzene according to the present invention.

The products were analyzed in an Agilent 6890N gas chromatograph with a flame ionization detector and a capillary column of INNOWAX, 60-m cross-linked methyl silicone with an internal diameter of 0.32 mm. FIG. 1 shows ethylbenzene conversion and diethylbenzene selectivity results obtained for the catalyst at a 400° C. reaction temperature, without pre-treating the catalyst. FIG. 2 shows ethylbenzene conversion and diethylbenzene selectivity results obtained at the same reaction temperature after pretreating the catalyst. The compositional analysis results for the reaction products show the reproducibility of the conversion reaction within ±1%. The product composition of both the treated and the untreated samples at a 400° C. reaction temperature for a reaction time of twenty seconds are shown in Table 2 below.

TABLE 2

Product Compositions of Untreated and treated Samples

| | Product Composition | |
| --- | --- | --- |
| Component | Untreated sample | Treated sample |
| Gases (wt %) | 7.46 | 4.13 |
| Benzene (wt %) | 19.77 | 10.96 |
| Toluene (wt %) | 4.49 | 2.46 |
| Xylene (wt %) | 1.43 | 1.02 |
| Ethyl toluene (wt %) | 2.44 | 2.56 |
| Diethylbenzene (wt %) | 9.13 | 20.50 |
| Triethylbenzene (wt %) | 0.28 | 0.37 |

Example 2

Figure 3:
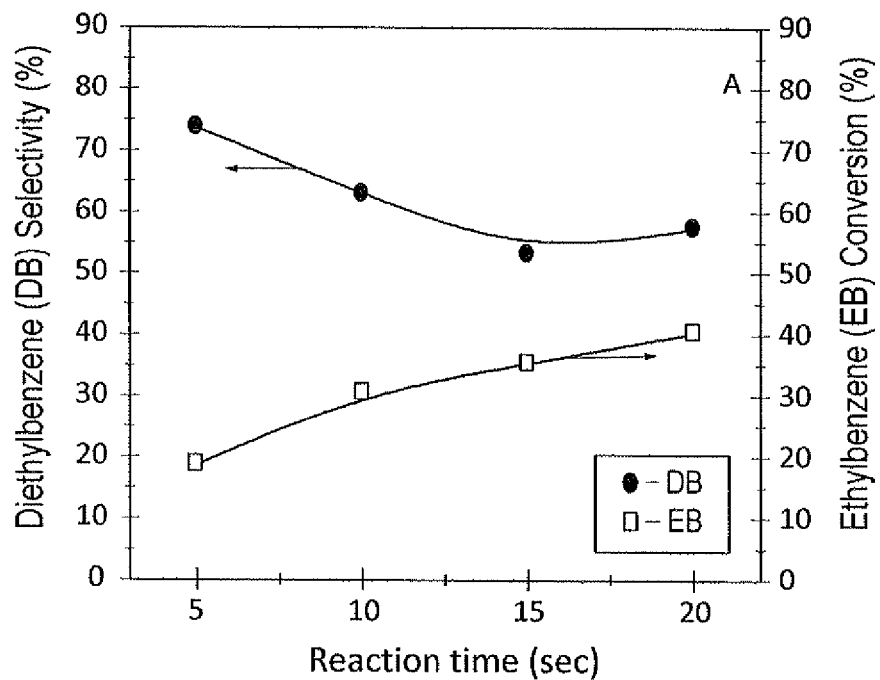
FIG. 3 is a graph illustrating ethylbenzene conversion and diethylbenzene selectivity as a function of reaction time at 350° C. reaction temperature without zeolite pretreatment as a function of reaction time.
Figure 4:
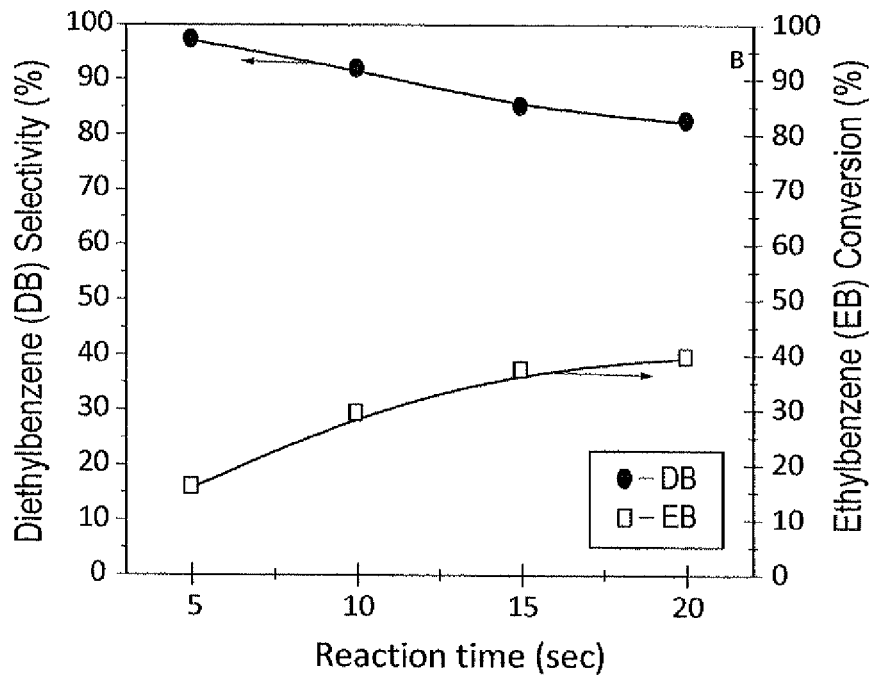
FIG. 4 is a graph illustrating ethylbenzene conversion and diethylbenzene selectivity as a function of reaction time at 350° C. reaction temperature following zeolite pretreatment in accordance with a method of making diethylbenzene according to the present invention.

In a second example, the production of diethylbenzene from the alkylation reaction of ethylbenzene and ethanol using the catalysts as prepared as described in Example 1 at a 350° C. reaction temperature was studied. Following the procedure of the first example for evaluation of the catalyst, the alkylation reaction was carried out at 350° C. The reaction conditions and product analysis conditions were similar to those described above with regard to the first example. FIG. 3 shows ethylbenzene conversion and diethylbenzene selectivity results obtained for the catalyst at a 350° C. reaction temperature, without pretreating of the catalyst. FIG. 4 shows ethylbenzene conversion and diethylbenzene selectivity results obtained at the same reaction temperature after pretreating the catalyst. The thermodynamic equilibrium composition of the three diethylbenzene isomers at 350° C., for a reaction time of seconds, without pretreatment and after pretreatment are as follows: ortho-diethylbenzene:meta-diethylbenzene:para-diethylbenzene=9:62:29 and 6:63:31, respectively. The product composition of both the treated and the untreated samples at a 350° C. reaction temperature for a reaction time of twenty seconds are shown in Table 3 below.

TABLE 3

Product Compositions of Untreated and Treated Samples

| | Product Composition | |
|---|---|---|
| Component | Untreated Sample | Treated Sample |
| Gases (wt %) | 1.40 | 0.17 |
| Benzene (wt %) | 9.83 | 4.70 |
| Toluene (wt %) | 1.85 | 0.93 |
| Xylene (wt %) | 0.74 | 0.45 |
| Ethyl toluene (wt %) | 2.47 | 1.81 |
| Diethylbenzene (wt %) | 23.15 | 32.50 |
| Triethylbenzene (wt %) | 0.56 | 0.30 |

Comparing the data in FIGS. 2 and 3 at reaction temperatures of 350° C. and 400° C., it can be seen that high diethylbenzene selectivity (~97%) is obtained at a reaction temperature of 350° C. It can be further seen that the ZSM-5 zeolite catalyst is highly selective towards diethylbenzene.

It is to be understood that the present invention is not limited to the embodiments described above, but encompasses any and all embodiments within the scope of the following claims.

We claim:

1. A method of making diethylbenzene, comprising the steps of:
   heating a zeolite catalyst in argon gas in a reaction chamber;
   selectively coking the zeolite catalyst with a precursor mixture of ethylbenzene and ethanol;
   flowing the argon gas over the coked zeolite catalyst;
   injecting a feedstock mixture of ethylbenzene and ethanol into the reaction chamber to produce diethylbenzene; and
   removing the diethylbenzene from the reaction chamber.

2. The method of making diethylbenzene as recited in claim 1, wherein the catalyst comprises a catalyst selected from the group consisting of mordenite, beta, ZSM-5, ZSM-11, ZSM-12, ZSM-22, ZSM-23, SAPO-5, SAPO-34, SAPO-11 and MAPO-36.

3. The method of making diethylbenzene as recited in claim 2, wherein the catalyst is a zeolite catalyst having a silica-to-alumina molar ratio between about 23 and about 80.

4. The method of making diethylbenzene as recited in claim 1, wherein the catalyst comprises ZSM-5 zeolite catalyst.

5. The method of making diethylbenzene as recited in claim 4, wherein the step of heating the catalyst comprises heating the catalyst at a temperature of about 620° C. for approximately 15 minutes in a flow of argon gas.

6. The method of making diethylbenzene as recited in claim 5, wherein the precursor mixture of ethylbenzene and ethanol comprises a mixture of ethylbenzene and ethanol in a molar ratio of 1 to 1.

7. The method of making diethylbenzene as recited in claim 6, wherein the step of selectively coking the catalyst with the precursor mixture of ethylbenzene and ethanol comprises selectively coking the catalyst with the precursor mixture of ethylbenzene and ethanol at a temperature between 250° C. and 400° C. for between 5 seconds and 20 seconds.

8. The method of making diethylbenzene as recited in claim 7, wherein the feedstock mixture of ethylbenzene and ethanol comprises a mixture of ethylbenzene and ethanol in a molar ratio of 1 to 1.

9. The method of making diethylbenzene as recited in claim 8, wherein the step of injecting the reaction mixture of ethylbenzene and ethanol into the reaction chamber further comprises heating the reaction chamber to a temperature between approximately 250° C. and approximately 400° C.

10. The method of making diethylbenzene as recited in claim 9, wherein the step of injecting the reaction mixture of ethylbenzene and ethanol into the reaction chamber further comprises maintaining a gas pressure within the reaction chamber between 1.0 atmospheres and 5.0 atmospheres.

11. A method of making diethylbenzene, comprising the steps of:
    heating a reactor chamber containing ZSM-5 catalyst in a flow of argon gas;
    selectively coking the ZSM-5 catalyst with a precursor mixture of ethylbenzene and ethanol in a molar ratio about 1:1;
    flowing the argon gas over the coked zeolite catalyst;
    injecting a feedstock mixture of ethylbenzene and ethanol into the reaction chamber at a temperature between 250° C. and 400° C. and a pressure between 1.0 and 5.0 atmospheres to produce diethylbenzene; and
    removing the diethylbenzene from the reaction chamber.

12. The method of making diethylbenzene according to claim 11, wherein said reactor chamber is disposed in a fast fluidized-bed reactor.

13. The method of making diethylbenzene according to claim 11, wherein said step of heating the reactor chamber comprises heating the reactor chamber at about 650° C. for about 15 minutes.

14. The method of making diethylbenzene according to claim 11, wherein said step of selectively coking the ZSM-5 catalyst comprises injecting the precursor mixture into the reactor chamber and heating the precursor mixture at between 250° C. and 400° C. for between 5 seconds and 20 seconds.

15. The method of making diethylbenzene according to claim 11, wherein said step of selectively coking the ZSM-5 catalyst comprises depositing coke derived from heating the precursor material onto the ZSM-5 catalyst to between about 0.7 wt % to about 1.5 wt % of the total weight of the catalyst.

16. The method of making diethylbenzene according to claim 11, wherein said feedstock comprises a mixture of ethylbenzene and ethanol in a molar ratio of 1:1.

* * * * *